United States Patent
Chuang

(10) Patent No.: US 9,070,317 B2
(45) Date of Patent: Jun. 30, 2015

(54) DEVICE AND METHOD OF AUTOMATIC DISPLAY BRIGHTNESS CONTROL

(71) Applicant: Quanta Computer Inc., Taoyuan Shien (TW)

(72) Inventor: Tung-Lin Chuang, New Taipei (TW)

(73) Assignee: QUANTA COMPUTER INC., Guishan Dist., Taoyuan (TW)

(*) Notice: Subject to any disclaimer, the term of this patent is extended or adjusted under 35 U.S.C. 154(b) by 102 days.

(21) Appl. No.: 14/070,337

(22) Filed: Nov. 1, 2013

(65) Prior Publication Data

US 2015/0009121 A1   Jan. 8, 2015

(30) Foreign Application Priority Data

Jul. 4, 2013   (TW) .............................. 102124022 A

(51) Int. Cl.
*G09G 5/10*   (2006.01)
*G06F 3/01*   (2006.01)
*G06F 3/00*   (2006.01)

(52) U.S. Cl.
CPC *G09G 5/10* (2013.01); *G06F 3/015* (2013.01); *G06F 3/002* (2013.01); *G09G 2380/08* (2013.01); *G09G 2320/0626* (2013.01); *G09G 2354/00* (2013.01)

(58) Field of Classification Search
CPC ............. G06F 3/01; G06F 3/013; H04N 7/15; A61B 5/0402; G04G 5/00; G04B 19/24
See application file for complete search history.

(56) References Cited

U.S. PATENT DOCUMENTS

| | | | |
|---|---|---|---|
| 2008/0027339 A1* | 1/2008 | Nagai et al. .................. | 600/509 |
| 2013/0121116 A1* | 5/2013 | Lee ................................. | 368/21 |
| 2013/0127980 A1* | 5/2013 | Haddick et al. ............ | 348/14.08 |

* cited by examiner

*Primary Examiner* — Michael Faragalla
(74) *Attorney, Agent, or Firm* — Sawyer Law Group, P.C.

(57) ABSTRACT

A device and a method of automatic display brightness control are provided. Human fatigue index and environmental factors for dry eyes are combined as an indicator to dynamically adjust the display brightness. Heart rate variability (HRV) is used as the human fatigue index, and the environmental $CO_2$ concentration is used as the environmental factors for dry eyes here.

9 Claims, 3 Drawing Sheets

DEVICE AND METHOD OF AUTOMATIC DISPLAY BRIGHTNESS CONTROL

CROSS-REFERENCE TO RELATED APPLICATION

This application claims the priority benefit of Taiwan application serial no. 102124022, filed Jul. 4, 2013, the full disclosure of which is incorporated herein by reference.

FIELD OF THE INVENTION

The disclosure relates to a device and a method of display brightness control. More particularly, the disclosure relates to a device and a method of automatic display brightness control.

BACKGROUND

In today's digital era, the use and operation of computers has become an unavoidable task. With intense global competition, the use of the computer has become heavier. Computer-related health problems have annoyed the modern people and even harmed life. Eyes are the window of human souls. However, long-time use of computers can let people ignore that the less blink times of eyes and poor quality of air can decrease the normal rinse effect of the eyes. For serious conditions, it can produce eye inflammation or retinal vascular occlusion. Therefore, the eye health has become a serious problem for using computers. At present, studies about sick building syndrome and computers terminal syndrome have revealed that carbon dioxide concentration and physical fatigue after long-time using computers can make eyes feel dry and photophobia.

SUMMARY

In one aspect, the current invention is directed to a device and a method of automatic display brightness control. Human fatigue index and environmental factors for dry eyes are combined as an indicator to dynamically adjust the display brightness to fit the current physiological state of a user. Therefore, the harm made by improper computer operation behavior to user's eyes can be initiatively improved. Heart rate variability (HRV) is used as the human fatigue index, and the environmental $CO_2$ concentration is used as the environmental factors for dry eyes here.

The automatic display brightness control device above comprises a display, a carbon dioxide sensor, an electrocardiographic electrode, and a calculating device. The carbon dioxide sensor above is used for detecting an environmental carbon dioxide concentration $[CO_2]$. The electrocardiographic electrode can be used to measure an electrocardiography of a user. The calculating device above is used to receive the carbon dioxide concentration $[CO_2]$ and the electrocardiography to calculate a weighted value A of the carbon dioxide concentration $[CO_2]$ and a weighted value B of heart rate variability (HRV), whereby a display brightness adjustment index Z and an adjusted display brightness Dadj are calculated and used to adjust display brightness of the display, wherein Z is equal to $C_1 \times A + C_2 \times B$, $C_1$ is ranged from 1 to 5, and $C_2$ is ranged from 1 to 10.

The automatic display brightness control method comprises the following steps.

First, a weighted value A of the carbon dioxide concentration $[CO_2]$ is calculated. An environmental carbon dioxide concentration $[CO_2]$ is measured, and X value is calculated. X is equal to $([CO_2]-300)/100$. Subsequently, the weighted value A is 0 when X<0, and the weighted value A is an integer value of X plus 1 when X≥0.

Next, a weighted value B of heart rate variability (HRV) is calculated. A numeric sequence of RR interval in an electrocardiogram of a user is retrieved. Then, a spectral analysis of the numeric sequence of the RR interval is performed by fast Fourier transformation to obtain amplitudes of sympathetic nerves (LF, 0.04-0.15 Hz) and parasympathetic nerves (HF, 0.15-0.4 Hz). A current balance index (LF/HF)now of sympathetic nerves and parasympathetic nerves is calculated. An enhanced balance index Y is next calculated. Y is equal to $[(LF/HF)now-(LF/HF)prev]2$, wherein the (LF/HF)prev is a previous balance index. Then, a threshold value of the enhanced balance index Y is calculated. The threshold value of Y is equal to an average value of previous 30 enhanced balance index Ys. Finally, the weighted value B of heart rate variability is 1 when the enhanced balance index Y is greater than the threshold value of the enhanced balance index Y, and the weighted value B is 0 when the enhanced balance index Y is smaller or equal to the threshold value of the enhanced balance index Y.

Finally, an adjusted display brightness Dadj is calculated. Dadj is equal to $0.9975 \times Dnow \times Z$, and Dnow is a current brightness of the display.

It is to be understood that both the foregoing general description and the following detailed description are by examples, and are intended to provide further explanation of the invention as claimed. The foregoing currents a simplified summary of the disclosure in order to provide a basic understanding to the reader. This summary is not an extensive overview of the disclosure and it does not identify key/critical elements of the current invention or delineate the scope of the current invention. Its sole purpose is to current some concepts disclosed herein in a simplified form as a prelude to the more detailed description that is currented later. Many of the attendant features will be more readily appreciated as the same becomes better understood by reference to the following detailed description considered in connection with the accompanying drawings.

DETAILED DESCRIPTION

Figure 1:
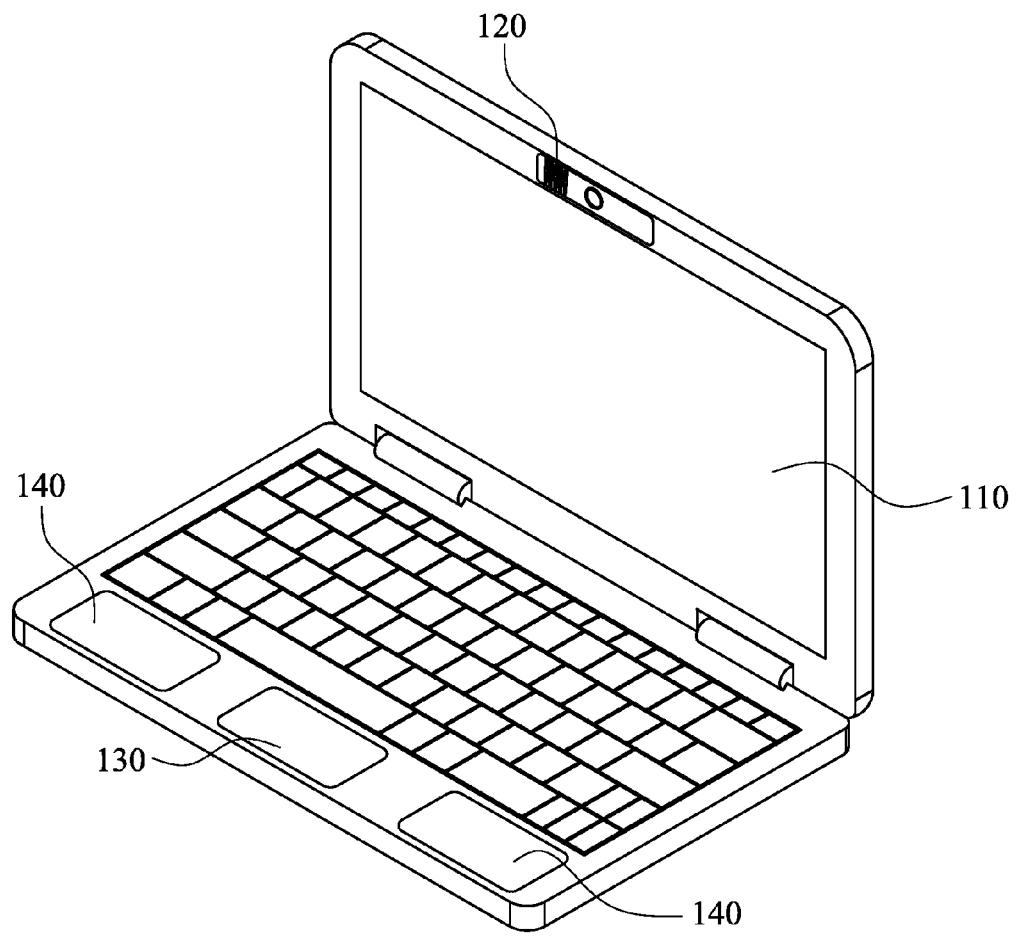
FIG. 1 is a diagram of a notebook computer having an automatic display brightness control device according to one embodiment of this invention.

Accordingly, a device and a method of automatic display brightness control are provided. Human fatigue index and environmental factors for dry eyes are combined as an indicator to dynamically adjust the display brightness to make the user's eyes more comfortable. In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 is a diagram of a notebook computer having an automatic display brightness control device according to one embodiment of this invention. In FIG. 1, a carbon dioxide sensor 120 is disposed on a display 110 of a notebook computer 100, and two electrocardiographic electrodes 140 are respectively disposed on two sides of a touch pad 130. The carbon dioxide sensor 120 is used for detecting an environmental carbon dioxide concentration [CO2] around a user of the notebook 100. The two electrocardiographic electrodes 140 are used to measure an electrocardiography of the user through the user's wrist pulse to obtain a fatigue index of the user according to the physiological state of the user.

Although a notebook computer 100 is taken as an example in FIG. 1, the carbon dioxide detector 120 and the electrocardiographic electrodes 140 also can be mounted on a personal computer (PC), a tablet computer, a mobile device, and a communication device or any other electronic devices having a display. For example, in the case of PC, the carbon dioxide sensor 120 can be disposed on a display of a PC, and the electrocardiographic electrodes 140 can be disposed on two sides of a keyboard of the PC. Or, the electrocardiographic electrodes 140 don't need to be integrated into the PC, and an electrocardiography can be transferred to the PC through a wired or wireless transmission.

Figure 2:
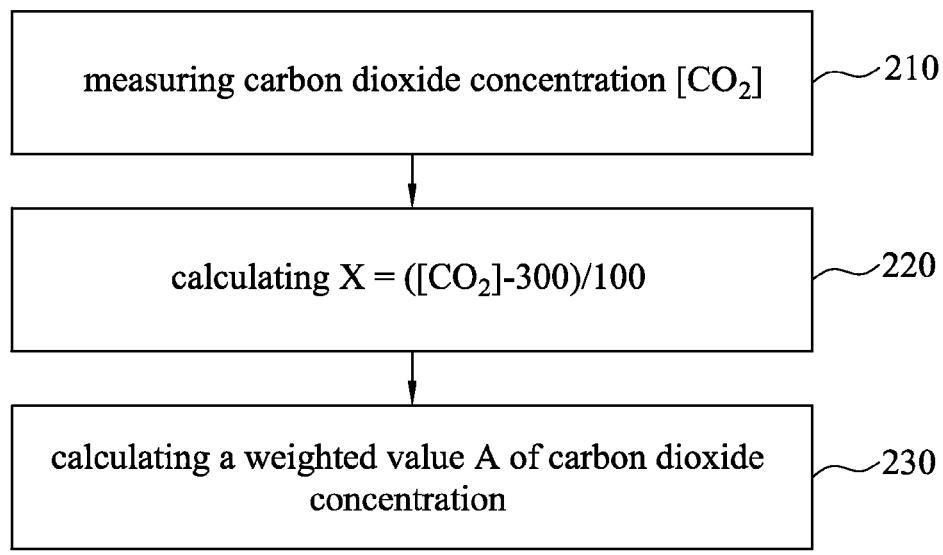
FIG. 2 is a process flow diagram of calculating a weighted value A of the carbon dioxide concentration $[CO_2]$.

FIG. 2 is a process flow diagram of calculating a weighted value A of the carbon dioxide concentration [CO2]. In step 210, the environmental carbon dioxide concentration [CO2] (unit ppm) is measured first. When the environmental carbon dioxide concentration [CO2] is greater than 2000 ppm, a human staying one to two hours in this environment will have a risk of death. Therefore, the maximum measured carbon dioxide concentration is limited to 2000 ppm.

In step 220, the measured carbon dioxide concentration minus the outdoor carbon dioxide concentration (300 ppm), and then is divided by 100 to get the X value.

In step 230, the weighted value A of the carbon dioxide concentration [CO2] is calculated. The weighted value A is 0 when X<0, and the weighted value A is an integer value of X plus 1 when X≥0. Therefore, the value of A will be an integer from 0 to 18.

Figure 3:
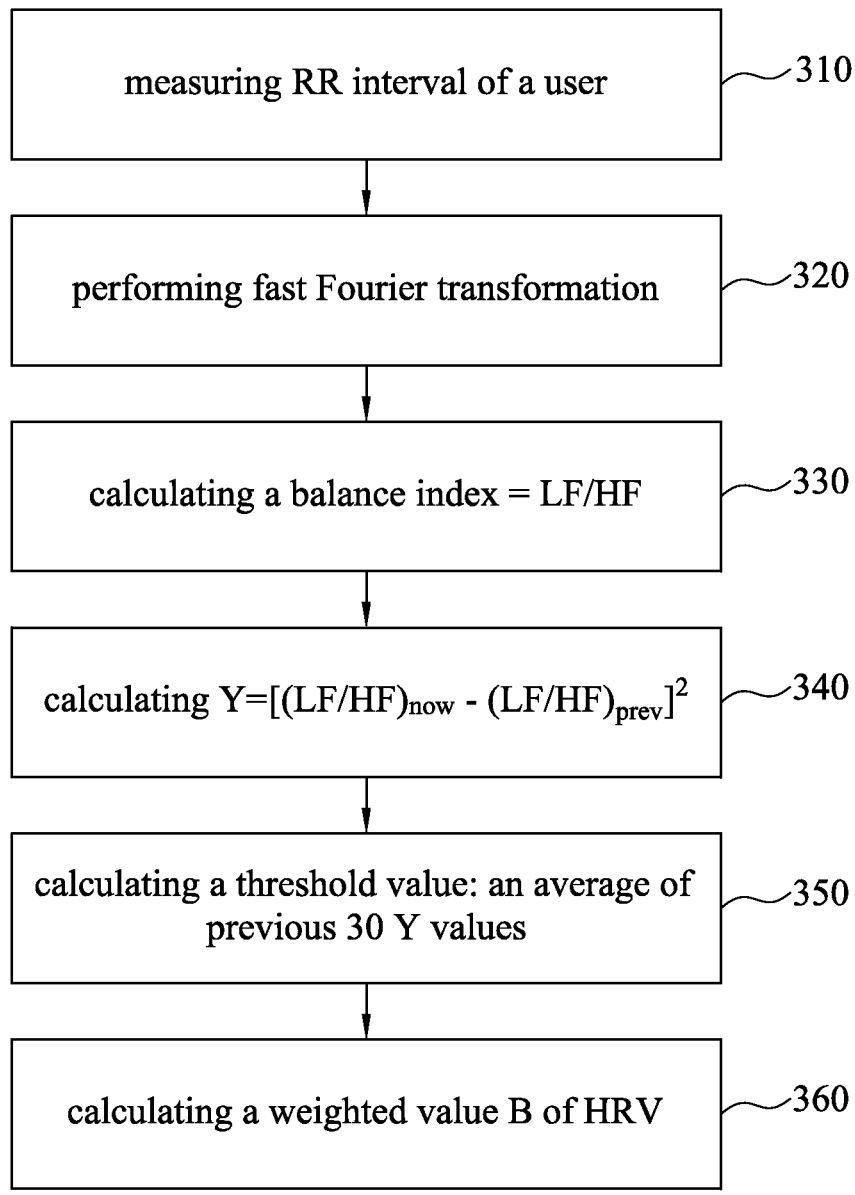
FIG. 3 is a process flow diagram of calculating a weighted value B of heart rate variability.

FIG. 3 is a process flow diagram of calculating a weighted value B of heart rate variability. Since heart rate variability (HRV) refers to small differences between continuous electrocardiogram R wave heartbeat interval period, and heart rate is regulated by the autonomic nervous system (including the sympathetic and parasympathetic nerves). Therefore, HRV can be recurrented by a balance index of the sympathetic nerves/the parasympathetic nerves (LF/HF). Here, the calculation method of HRV is referred to a publication of Huang Wen Tseng (Perception of fatigue driving patron design study, 2010 International Conference on Advanced Information Technologies, (AIT2010), pp. 206 (ISBN:978-986-7043-30-6)), which is incorporated herein entirely by reference.

In step 310, electrocardiographic electrodes 140 are used to measure electrocardiography of a user. A numeric sequence of RR interval in the electrocardiogram of the user is obtained by measuring the time interval between neighboring R wave peaks.

In step 320, the obtained numeric sequence of RR interval is analyzed by spectral analysis (i.e. fast Fourier transformation; FFT) to respectively obtain the amplitude of sympathetic nerves (low frequency LF, 0.04-0.15 Hz) and the parasympathetic nerves (high frequency HF, 0.15-0.4 Hz).

In step 330, the value of the LF amplitude over the HF amplitude is calculated to obtain a current balance index of the sympathetic nerves/the parasympathetic nerves, (LF/HF) now.

In step 340, an enhanced balance index Y is calculated. Y is equal to [(LF/HF)now−(LF/HF)prev]2, wherein the (LF/HF) prev is a previous balance index.

In step 350, a threshold value of the enhanced balance index Y is calculated. The threshold value of Y is equal to an average value of previous 30 enhanced balance index Ys.

In step 360, the weighted value B of heart rate variability is calculated. The weighted value B of heart rate variability is 1 when the enhanced balance index Y is greater than the threshold value of the enhanced balance index Y, and the weighted value B is 0 when the enhanced balance index Y is smaller or equal to the threshold value of the enhanced balance index Y.

Next, a display brightness adjustment index Z is determined by the following equation (1). In equation (1), A and B are the weighted values of carbon dioxide concentration and HRV, respectively. Both C1 and C2 are determined by the user according to personal physiological sensitivity to the carbon dioxide concentration and the influence degree of personal physical fatigue. C1 is ranged from 1 to 5, and C2 is ranged from 1 to 10.

$$Z = C1 \times A + C2 \times B \tag{1}$$

Therefore, the value of Z can be feedback to the notebook computer 100. Then, the notebook computer 100 can adjust its display brightness according to the Z value. In order to avoid the negative effect of the over dark of the display brightness after adjusting the display brightness, the 75% of the current display brightness (Dnow) is the lower limit of the adjusted display brightness (Dadj). The adjusted display brightness (Dadj) can be calculated by the following equation (2).

$$Dadj = Dnow - Dnow \times (1 - 0.75)/100 \times Z \tag{2}$$
$$= 0.9975 \times Dnow \times Z$$

In one embodiment, the notebook computer 100 can further comprise a calculating device (not shown in FIG. 1), such as a central processing unit (CPU) to receive the carbon dioxide concentration and the electrocardiography to calculate the weighted value of the carbon dioxide concentration and the weighted value B of heart rate variability, whereby to calculate the display brightness adjustment index Z and the adjusted display brightness (Dadj) to adjust the display brightness of the notebook computer 100.

According to the device and the method of automatic display brightness control above, a carbon dioxide sensor and an electrocardiographic electrode can be disposed surrounding a display to respectively detect an environmental carbon dioxide concentration and the user's electrocardiography. Then, the display brightness can be automatically adjusted according to the environmental carbon dioxide concentration and the user's physiological state. Thus, various physiological discomfort caused by long-time watching the display can be reduced.

All the features disclosed in this specification (including any accompanying claims, abstract, and drawings) may be replaced by alternative features serving the same, equivalent or similar purpose, unless expressly stated otherwise. Thus, each feature disclosed is one example only of a generic series of equivalent or similar features.

What is claimed is:

1. An automatic display brightness control device, the device comprising:
  a display;

a carbon dioxide sensor for detecting an environmental carbon dioxide concentration $[CO_2]$;

an electrocardiographic electrode for measuring an electrocardiography of a user; and a calculating device for receiving the carbon dioxide concentration $[CO_2]$ and the electrocardiography to calculate a weighted value A of the carbon dioxide concentration $[CO_2]$ and a weighted value B of heart rate variability (HRV), whereby a display brightness adjustment index Z and an adjusted display brightness $D_{adj}$ are calculated and used to adjust display brightness of the display, wherein Z is equal to $C1 \times A + C2 \times B$, C1 is ranged from 1 to 5, and C2 is ranged from 1 to 10.

2. The device of claim 1, wherein the weighted value A of the carbon dioxide concentration $[CO_2]$ is calculated by a method comprising:

calculating X value, which is equal to $([CO_2]-300)/100$; and calculating the weighted value A, which is equal to 0 when X<0, and an integer value of X plus 1 when X≥0.

3. The device of claim 1, wherein the weighted value B of heart rate variability is calculated by a method comprising:

retrieving a numeric sequence of RR interval in the electrocardiogram of the user;

performing a spectral analysis of the numeric sequence of the RR interval by fast Fourier transformation to obtain amplitudes of sympathetic nerves (LF, 0.04-0.15 Hz) and parasympathetic nerves (HF, 0.15-0.4 Hz);

calculating a current balance index $[(LF/HF)_{now}]$ of the sympathetic nerves and parasympathetic nerves, wherein the index is equal to an amplitude of LF over an amplitude of HF;

calculating an enhanced balance index Y, which is equal to $[(LF/HF)_{now}-(LF/HF)_{prev}]^2$, wherein the $(LF/HF)_{prev}$ is a previous balance index;

calculating a threshold value of the enhanced balance index Y, which is equal to an average value of previous 30 enhanced balance index Ys; and calculating the weighted value B of heart rate variability, wherein the weighted value B is equal to 1 when the enhanced balance index Y is greater than the threshold value of the enhanced balance index Y, and the weighted value B is equal to 0 when the enhanced balance index Y is smaller or equal to the threshold value of the enhanced balance index Y.

4. The device of claim 1, wherein the adjusted display brightness $D_{adj}$ is equal to $0.9975 \times D_{now} \times Z$, and $D_{now}$ is a current brightness of the display.

5. The device of claim 1, wherein the calculating device is a notebook computer, a tablet computer, a mobile device, or a communication device.

6. An automatic display brightness control method, the method comprising:

measuring an environmental carbon dioxide concentration $[CO_2]$;

measuring and recording an electrocardiography of a user;

receiving the environmental carbon dioxide concentration $[CO_2]$ and the electrocardiography;

calculating a weighted value A of the carbon dioxide concentration $[CO_2]$ and a weighted value B of heart rate variability; and calculating an adjusted display brightness $D_{adj}$ by the weighted value A of the carbon dioxide concentration $[CO_2]$ and the weighted value B of heart rate variability.

7. The method of claim 6, wherein the weighted value A of the carbon dioxide concentration $[CO_2]$ is calculated by a method comprising:

calculating X value, which is equal to $([CO_2]-300)/100$, and calculating the weighted value A, wherein the weighted value A is equal to 0 when the X<0, and the weighted value A is equal to an integer value of X plus 1 when the X≥0.

8. The method of claim 6, wherein the weighted value B of heart rate variability is calculated by a method comprising:

retrieving a numeric sequence of RR interval in the electrocardiogram of the user;

performing a spectral analysis of the numeric sequence of the RR interval by fast Fourier transformation to obtain amplitudes of sympathetic nerves (LF, 0.04-0.15 Hz) and parasympathetic nerves (HF, 0.15-0.4 Hz);

calculating a current balance index $[(LF/HF)_{now}]$ of the sympathetic nerves and parasympathetic nerves, wherein the index is equal to an amplitude of LF over an amplitude of HF;

calculating an enhanced balance index Y, which is equal to $[(LF/HF)_{now}-(LF/HF)_{prev}]^2$, wherein the $(LF/HF)_{prev}$ is a previous balance index;

calculating a threshold value of the enhanced balance index Y, which is equal to an average value of previous 30 enhanced balance index Ys; and calculating the weighted value B of heart rate variability, wherein the weighted value B is equal to 1 when the enhanced balance index Y is greater than the threshold value of the enhanced balance index Y, and the weighted value B is equal to 0 when the enhanced balance index Y is smaller or equal to the threshold value of the enhanced balance index Y.

9. The method of claim 6, wherein the adjusted display brightness $D_{adj}$ is calculated by a method comprising:

equaling a display brightness adjustment index Z to $C1 \times A + C2 \times B$, wherein C1 is ranged from 1 to 5, and C2 is ranged from 1 to 10; and equaling the adjusted display brightness $D_{adj}$ to $0.9975 \times D_{now} \times Z$, and $D_{now}$ is a current brightness of the display.

* * * * *